US007865977B2

(12) United States Patent
Rayl et al.

(10) Patent No.: US 7,865,977 B2
(45) Date of Patent: Jan. 11, 2011

(54) THERMAL GOGGLE LENS ASSEMBLY WITH EXTERNALLY VENTED CHAMBER

(75) Inventors: Eric L. Rayl, Woodinville, WA (US); Michael K. Reeves, Woodinville, WA (US)

(73) Assignee: Smith Optics, Inc., Ketchum, ID (US)

( * ) Notice: Subject to any disclaimer, the term of this patent is extended or adjusted under 35 U.S.C. 154(b) by 967 days.

(21) Appl. No.: 11/655,422

(22) Filed: Jan. 19, 2007

(65) Prior Publication Data

US 2007/0169252 A1 Jul. 26, 2007

Related U.S. Application Data

(60) Provisional application No. 60/761,058, filed on Jan. 20, 2006.

(51) Int. Cl.
*A61F 9/02* (2006.01)
(52) U.S. Cl. .......................................................... 2/435
(58) Field of Classification Search .............. 2/435–437
See application file for complete search history.

(56) References Cited

U.S. PATENT DOCUMENTS

| 1,562,350 | A |   | 11/1925 | Luckey |
|---|---|---|---|---|
| 2,321,159 | A | * | 6/1943 | Ryan .............................. 2/441 |
| 2,539,284 | A |   | 1/1951 | Thomas ............................ 2/14 |
| 2,665,686 | A |   | 1/1954 | Wood et al. .................... 128/41 |
| 3,012,248 | A |   | 12/1961 | Kleinman ......................... 2/14 |
| 3,267,807 | A | * | 8/1966 | Swope et al. ................. 359/890 |
| 3,377,626 | A |   | 4/1968 | Smith .............................. 2/14 |
| 3,488,215 | A |   | 1/1970 | Shepherd et al. ............ 117/124 |
| 3,505,680 | A |   | 4/1970 | Ring ............................... 2/14 |
| 3,591,864 | A |   | 7/1971 | Allsop ............................. 2/14 |
| 4,290,673 | A | * | 9/1981 | Yamamoto .................... 351/62 |
| 4,942,629 | A |   | 7/1990 | Stadlmann ..................... 2/435 |
| 5,018,223 | A |   | 5/1991 | Dawson et al. ................. 2/436 |
| 5,371,555 | A | * | 12/1994 | Nagel ........................... 351/57 |
| 5,517,700 | A | * | 5/1996 | Hoffman ....................... 2/428 |
| 6,009,564 | A |   | 1/2000 | Tackles ......................... 2/436 |
| 6,611,966 | B1 | * | 9/2003 | Yamamoto et al. ............. 2/436 |
| 7,126,732 | B2 | * | 10/2006 | McNeal et al. ................. 2/436 |
| 2001/0029623 | A1 |   | 10/2001 | Tsubooka ....................... 2/436 |
| 2003/0019017 | A1 |   | 1/2003 | Grau ............................ 351/41 |
| 2009/0044810 | A1 | * | 2/2009 | Kwok et al. ............ 128/206.28 |

FOREIGN PATENT DOCUMENTS

FR    2805155    8/2001
WO    WO00/61043    10/2000

* cited by examiner

*Primary Examiner*—Katherine Moran
(74) *Attorney, Agent, or Firm*—Dorsey + Whitney, LLP (57) ABSTRACT

A sports goggle includes double lens goggles having inner and outer lenses joined at their perimeter by an adhesive, such as silicone, to form an air cavity. A vent is formed on the outer lens to permit equalization of the air cavity with the environment. The vent includes a plug formed of a water impermeable and gas permeable material. An expansion member may insert within the plug to maintain the plug within the vent. In an alternative embodiment, a rivet having air channels formed therein secures a ring of permeable material to the lens.

35 Claims, 7 Drawing Sheets

THERMAL GOGGLE LENS ASSEMBLY WITH EXTERNALLY VENTED CHAMBER

CROSS-REFERENCE TO RELATED APPLICATION

This application claims the benefit of provisional application No. 60/761,058, filed Jan. 20, 2006, which is incorporated herein by reference.

TECHNICAL FIELD

This invention relates to thermal goggles and, more particularly, to double lens goggles.

BACKGROUND OF THE INVENTION

Goggles used for skiing tend to fog due to the low environmental temperature and the high humidity of the air captured between the goggles and a user's face. Fogging may be avoided by using goggles having inner and outer lenses defining an air cavity therebetween. The air cavity insulates the inner lens from the environment such that it does not become cold enough to cause condensation.

The air cavity typically must be vented such that changes in environmental pressure due to changes in altitude do not cause the lenses to bulge or break. In typical double lens goggles, the vent opens into the volume between the goggles and the user's face. Unfortunately, the air between the lens and the wearer's face is typically very moist, primarily because of the wearer's perspiration. As a result, air passing from the space behind the lens into the cavity between the lenses is laden with moisture which can condense on the inner surface of the outer lens.

A goggle could avoid introducing moisture laden air from behind the lens into the space between the lenses by venting the lens to the external environment through the outer lens. However, venting the inter-lens space through the outer lens tends to permit the entry of water through the vent into the space between the lens. Some goggles use a thin sheet of anhydrous material to cover a vent formed on the inner lens and thereby prevent the entry of water. However, the sheet is typically much larger than the vent and therefore occupies a substantial portion of the viewing area of the goggles. Furthermore, the thin anhydrous films are somewhat fragile and require complex housings such as are illustrated in U.S. Pat. No. 4,290,673 to Yamamoto.

In view of the foregoing it would be an advancement in the art to provide a compact, readily manufacturable vent for double lens goggles that reduces the possibility of fogging found in prior goggles.

SUMMARY OF THE INVENTION

According to one aspect of the invention, a goggle includes first and second lenses that cooperate to define an air cavity therebetween. The first lens is positioned between the second lens and a user's face. A shroud extends outwardly from the lenses and cooperates with the first lens and a user's face to define a second air cavity. A vent is formed in the second lens such that air passing through the vent is drawn from the environment rather than the second air cavity. The vent is obstructed by a plug that is air permeable and liquid water impermeable.

According to another aspect of the invention, the air permeable plug extends into the first air cavity and may abut the first lens. In a preferred embodiment, the plug is formed of sintered polyethylene, however other anhydrous or hydrophobic materials may be used. An expansion member may be inserted into the plug and urges the plug outwardly against the vent in order to retain the plug within the vent. The plug may have an aperture formed thereon sized to receive the plug. Alternatively, a permeable member having an aperture formed thereon is pinned to the vent by a resilient member. The resilient member includes a shaft insertable within the vent and having air channels formed therein. A cap may secure to the shaft and create a substantial seal such that air flowing into the vent by means of the air channels passes through the permeable member.

The lenses may be assembled by forming a vent in one of the lenses and applying a semi-liquid adhesive along a perimeter of one of the lenses. The lenses are then brought together and the adhesive is cured. The plug or other liquid impermeable structure is then positioned to obstruct the vent.

DETAILED DESCRIPTION OF PREFERRED EMBODIMENTS

Figure 1:
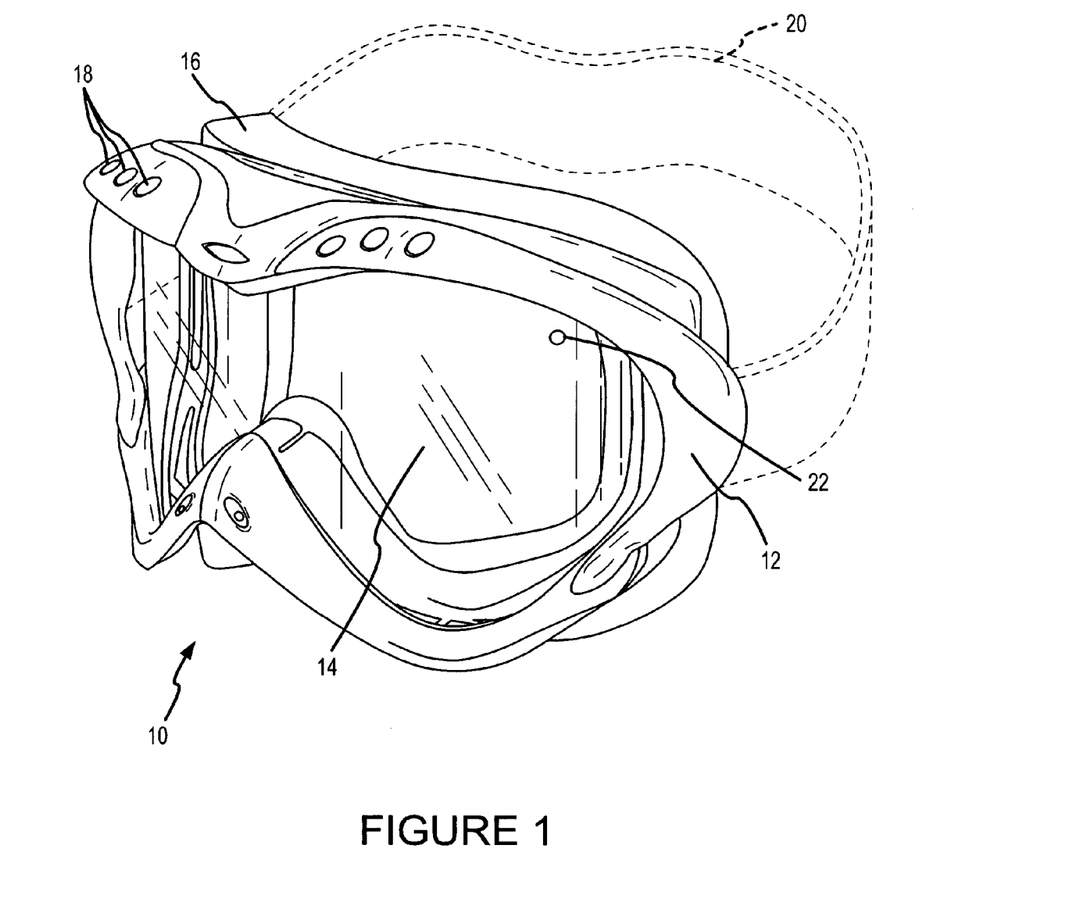
FIG. 1 is an isometric view of ski goggles in accordance with an embodiment of the present invention.

Referring to FIG. 1, goggles 10 include a frame 12 surrounding a lens 14. A rim 16 or shroud 16, typically formed of a deformable material, extends around the frame 12. A vent 18 may be formed in the frame to permit air to enter the space between the lens 14 and a user's face. In some goggles 10 the vent 18 is selectively openable and closable by a user in order to adjust the temperature of the air captured between the goggles 10 and the user's face. A strap 20 secured to the frame is positioned around a user's head to maintain the goggles against a user's face.

In the illustrated embodiment, the lens 14 is a double lens having inner and outer lenses. A vent 22 formed in either the inner or outer lens allows the pressure of the air cavity between the lenses to equalize with the environment. In the preferred embodiment, the vent 22 is formed in the outer lens such that air drawn into the air cavity comes from the environment and therefore has relatively low humidity, which is unlikely to cause fogging. The vent 22 is typically positioned to reduce interference with a user's field of vision. In one embodiment, the vent 22 is positioned at the center of the lens 14. In another, the vent 22 is positioned at the rear right or left edge of the lens.

Figure 2:
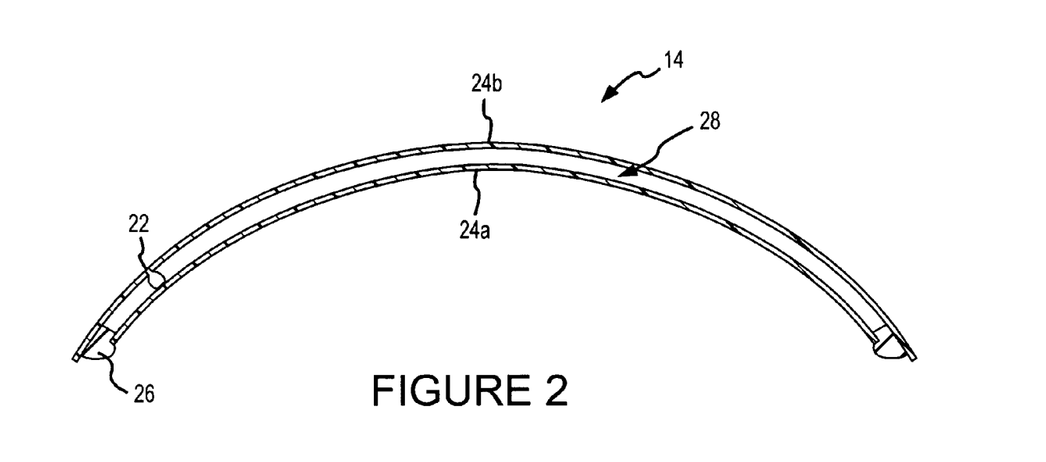
FIG. 2 is a cross-sectional view of a double lens assembly in accordance with an embodiment of the present invention.

Referring to FIG. 2, the lens 14 includes an inner lens 24a and an outer lens 24b. The lenses 24a, 24b tend to be curved to conform somewhat to a wearer's face. A seal 26 extends around the perimeter of the lenses 24a, 24b and cooperates with the lenses 24a, 24b to define an air cavity 28 substantially sealed from the environment, except for the vent 22. In a preferred embodiment, the seal 26 includes a silicone adhesive. In the illustrated embodiment, the outer lens 24b extends beyond the inner lens 24a and the seal 26 and the inner lens 24a is positioned within the perimeter defined by the seal 26. The outer lens 24b may include apertures, notches, or other features facilitating securement of the outer lens 24b to the frame 12.

Figure 3A:
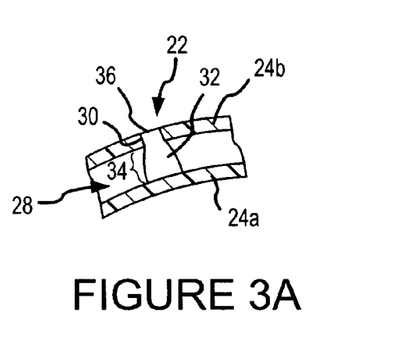
FIGS. 3A and 3B are partial cross-sectional views of vents in accordance with embodiments of the present invention.

Referring to FIG. 3A, in one embodiment, the vent 22 includes an aperture 30 formed in the outer lens 24b. A plug 32 is contained within the vent 22. The plug 32 may be formed of a resilient material such that an inner portion 34 of the plug 32 located within the air cavity 28 expands and aids in maintaining the plug 32 within the aperture 30. The plug 32 may also abut the inner lens 24a. The outer face 36 of the plug 32 may be flush with the outer surface of the outer lens 24b.

The plug 32 is preferably formed of a material that is water impermeable and gas permeable. The material may include PTFE such as a GORE-TEX membrane. In the preferred embodiment, the material of the plug 32 includes sintered polyethylene such as POREX Corporation's hydrophobic IRM-0595. Plugs 32 including sintered polyethylene having a pore size of between about 5 and 25 microns may advantageously be used.

Figure 3B:
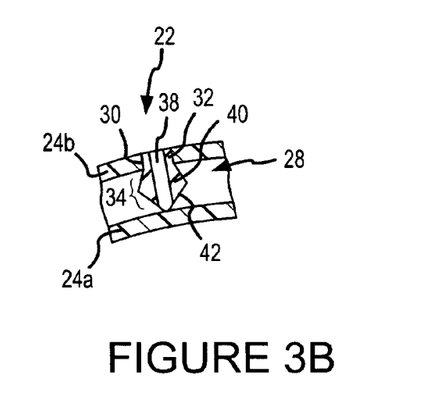

Referring to FIG. 3B, in one embodiment, the plug 32 includes an inner core 38 and a sheathe 40. The inner core 38 may be formed of a water impermeable and gas permeable material whereas the sheathe 40 is formed of an elastic material that is liquid impermeable and may also be gas permeable. Alternatively, the sheathe 40 is formed of a water impermeable and gas permeable material while the core 38 is formed of a liquid impermeable elastic material. Sintered polyethylene may have limited elasticity such that elastic core 38 or sheathe 40 may advantageously be used to bias the plug against the walls of the aperture 30 and/or to cause the inner portion 34 to expand within the air cavity 28. The base 42 of the plug may be angled, chamfered, scored, or contoured such that the core 38 is in fluid communication with the air cavity 28 even when the plug 32 is inserted such that it abuts the inner lens 24a. Alternatively, base 42 may be flat and the plug 32 may be inserted such that no substantial seal is created between the base 42 of the plug 32 and the inner lens 24a.

Figure 4:
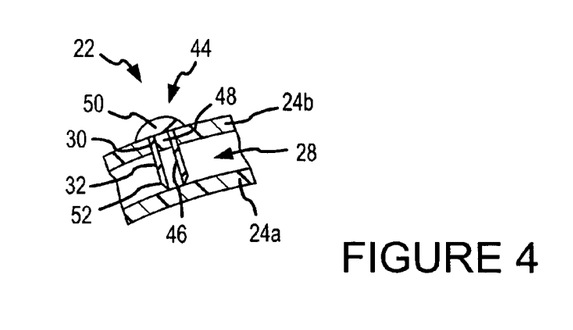
FIG. 4 is a partial cross-sectional view of an alternative vent in accordance with an embodiment of the present invention.

Referring to FIG. 4, in some embodiments, an expansion member 44 is used to secure the plug 32 within the aperture 30. The plug 32 may include an aperture 46 extending therethough to receive the expansion member 44. The expansion member 44 may include a shaft 48 sized to fit within the aperture 46 and a cap 50 secured to shaft 48. The shaft 48 may secure within the aperture 46 such that air is permitted to pass between the cap 50 and the outer lens 24b and contact the plug 32. The plug 32 may include a chamfered or tapered portion 52 to facilitate insertion into the aperture 30.

Figure 5:
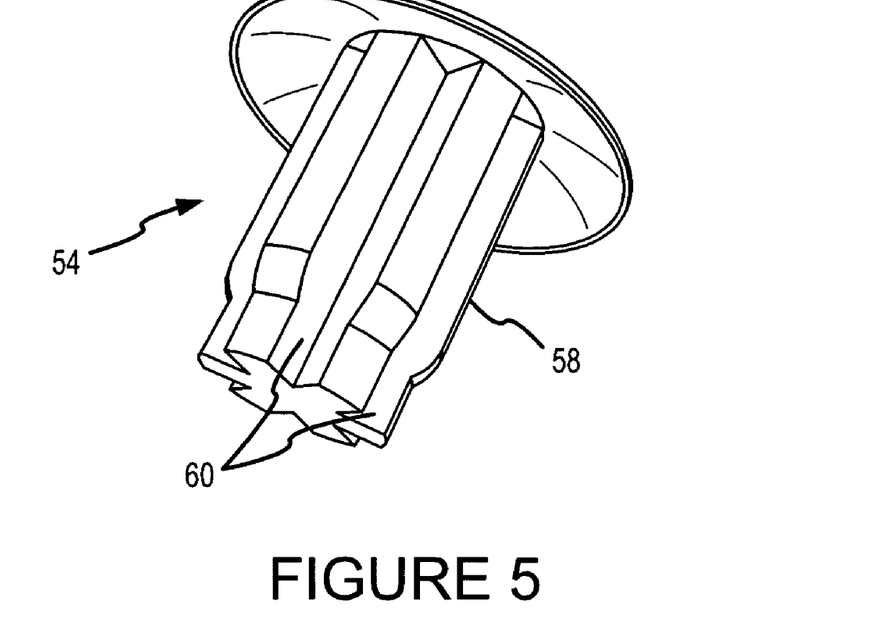
FIG. 5 is an isometric view of a rivet for mounting a permeable member to a vent in accordance with an embodiment of the present invention.
Figure 6:
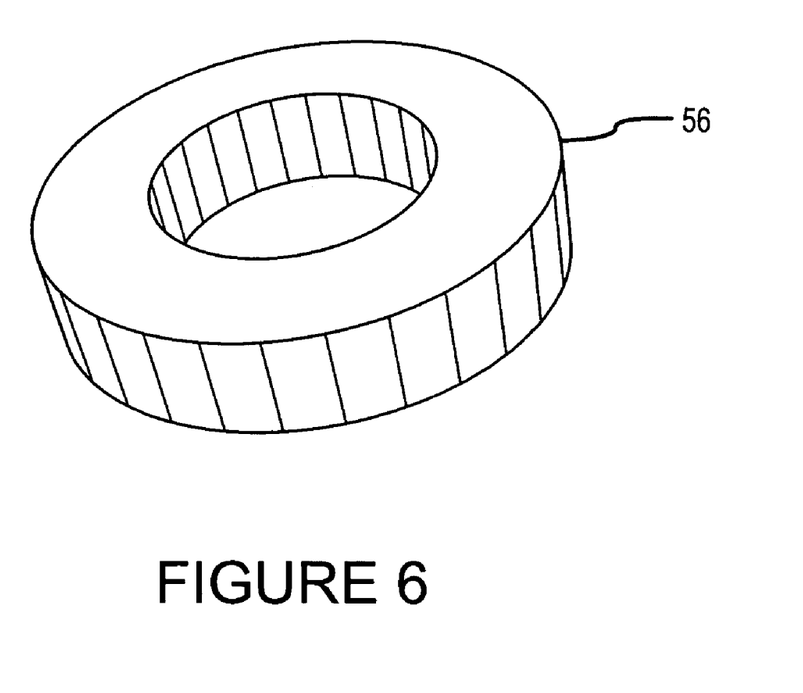
FIG. 6 is an isometric view of a permeable member in accordance with an embodiment of the present invention.
Figure 7:
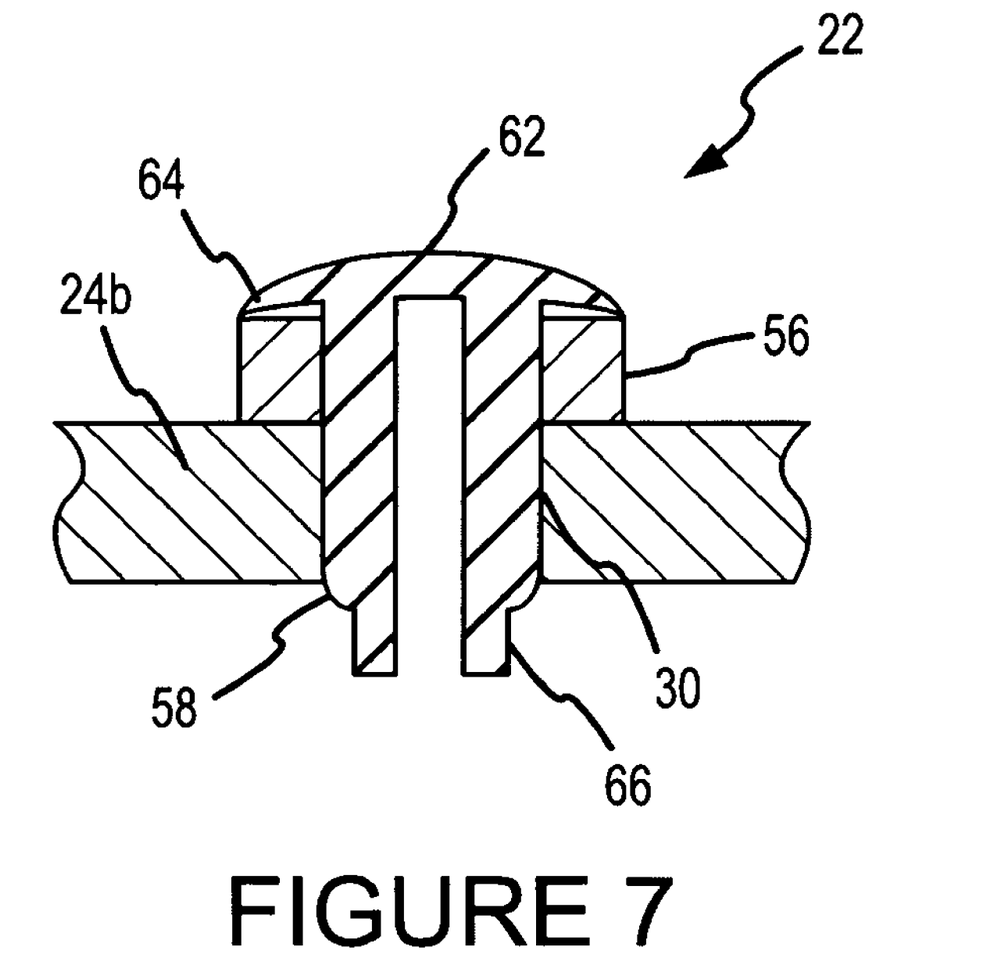
FIG. 7 is a cross-sectional view of a rivet and permeable member mounted to a vent in accordance with an embodiment of the present invention.

Referring to FIGS. 5-7, in another embodiment, a rivet 54 retains a ring 56 over the vent 22. The rivet 54 includes a shaft 58 having one or more air channels 60 formed therein. The air channels 60 may be in the form of one or more grooves extending along the shaft 58. As shown in FIG. 7, the ring 56 secures over the outer surface of one of the lenses 24a, 24b, preferably the outer lens 24b. A cap 62 secured to the shaft 58 may include a rim 64 extending around the upper edge of the ring 56 to retain the ring 56 and create a substantial seal between the rim 64 and the ring 56. Alternatively, the rim 64 may have a diameter smaller than the outer diameter of the ring 56 such that the rim 64 embeds itself within the ring 56 to create a substantial seal. The shaft 58 is preferably formed of a resilient material such that it may be forced into the aperture 30 and thereafter exert a restoring force against the wall of the aperture 30 to retain the shaft 58. In some embodiments, the shaft 58 may include a pawl, tab, or like structure engaging the lens 24b to retain the shaft 58 within the aperture 30, such that engagement with the aperture 30 does not substantially retain the shaft 58 within the aperture 30. The shaft 58 may include a tapered or chamfered portion 66 to facilitate insertion of the shaft 58 into the aperture 30.

Figure 8:
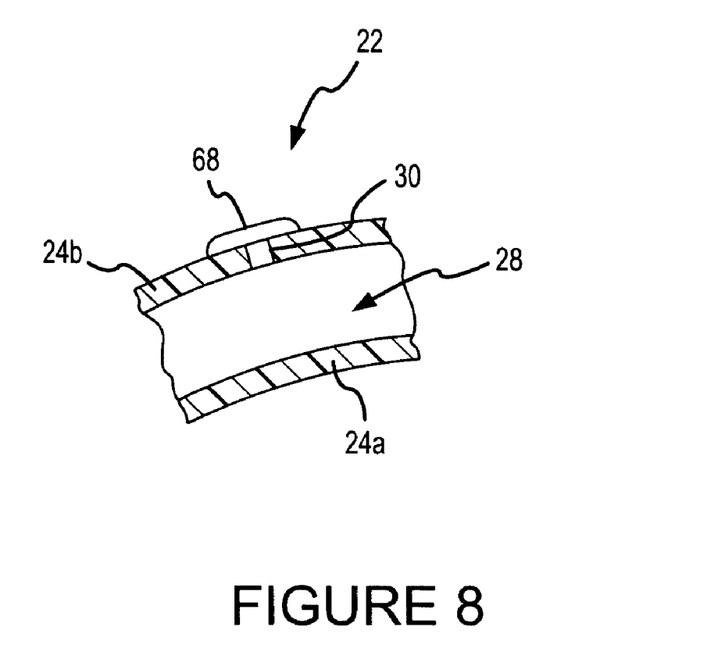
FIG. 8 is a partial cross-sectional view of another alternative vent in accordance with an embodiment of the present invention.

Referring to FIG. 8, in another embodiment, the vent 22 includes a patch 68 adhered to one of the lenses 24a, 24b, preferably the outer lens 24b. The patch 68 may advantageously be formed of sintered polyethylene, which is somewhat rigid and can be easily handled. However GORE-TEX or other anhydrous materials may also be used. The patch 68 may be secured to the lens 24a, 24b by means of adhesive extending around the aperture 30. The adhesive may be applied to the lens 24a, 24b or the patch 68 prior to attaching the patch 68 to the lens 24a, 24b.

Figure 9:
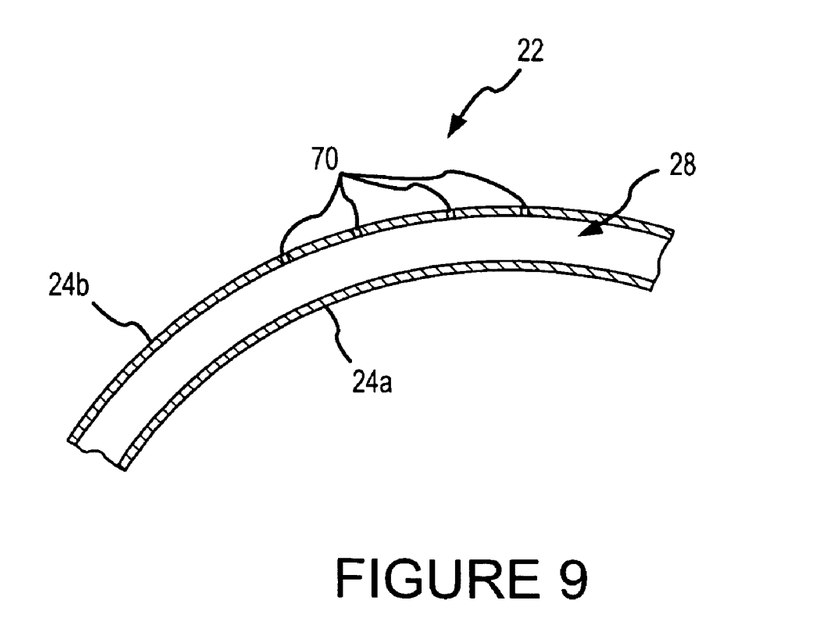
FIG. 9 is a partial cross-sectional view of another alternative vent in accordance with an embodiment of the present invention.

Referring to FIG. 9, in another embodiment the vent 22 is embodied as one or more micro-holes 70. The holes 70 typically have a size such that liquid water does not readily pass through them. The holes 70 may be formed by laser drilling or like means. The holes 70 may have a diameter between 1 and 25 microns, preferably between 5 and 15 microns.

Figure 10A:
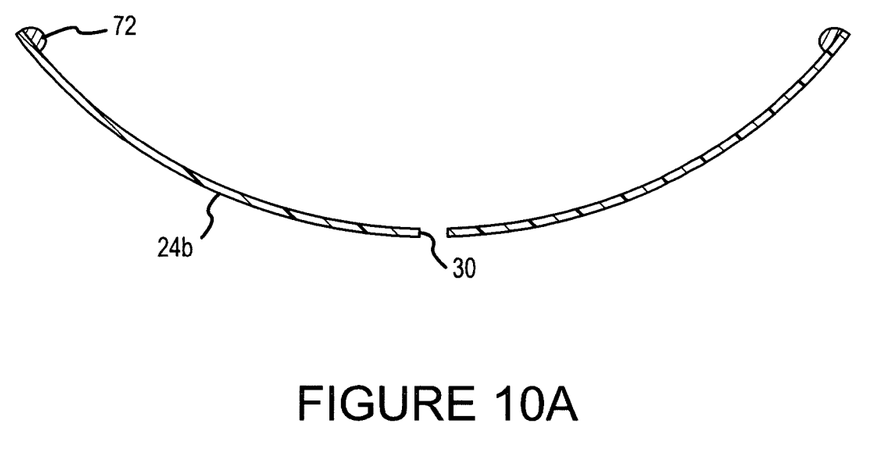
FIGS. 10A and 10B are cross-sectional views of goggle lenses illustrating a method for manufacturing a double lens assembly in accordance with an embodiment of the present invention.
Figure 10B:
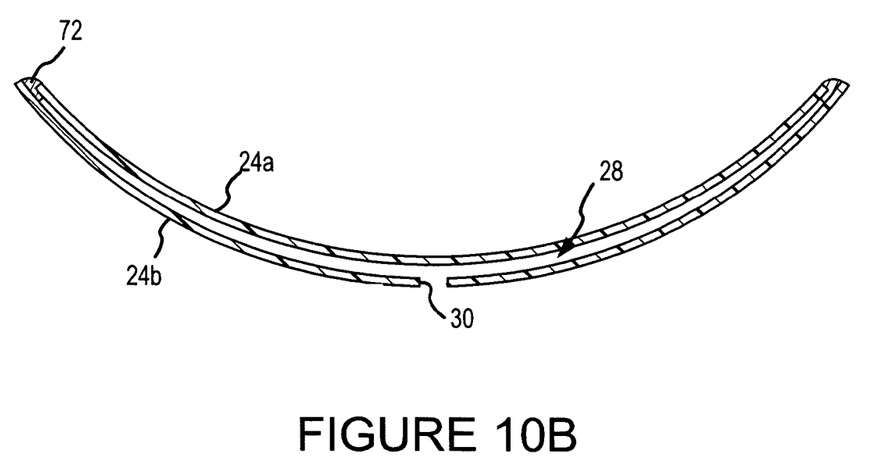

FIGS. 10A and 10B illustrate one embodiment of a method for forming double lens goggles. The lenses 24a, 24b may be joined by first placing a bead 72 of a semi-liquid adhesive on one of the lenses 24a, 24b. The bead 72 is typically formed of a silicone adhesive. Referring to FIG. 10B, the other lens 24a, 24b is then brought into contact with the bead 72. In a preferred embodiment, the bead 72 is formed on the outer lens 24b. The bead 72 may define a perimeter that is approximately the size of the perimeter of the inner lens 24a. In a preferred embodiment the aperture 30 is formed in either of the lenses 24a, 24b, preferably the outer lens 24b, prior to contacting both lenses 24a, 24b to the bead 72 of adhesive. Forming the vent prior to joining the lenses is advantageous when using a semi-liquid adhesive inasmuch as gases are allowed to escape through the aperture 30 and are less likely to cause the bead 72 to shift due to changes in the relative pressure of the air cavity 28 caused by changes in temperature and environmental pressure while the bead 72 of adhesive is being cured. Preferably after the bead 72 of adhesive is cured, the aperture 30 may be rendered substantially impervious to liquid entry using any of the structures described in FIGS. 1-9.

Figure 11A:
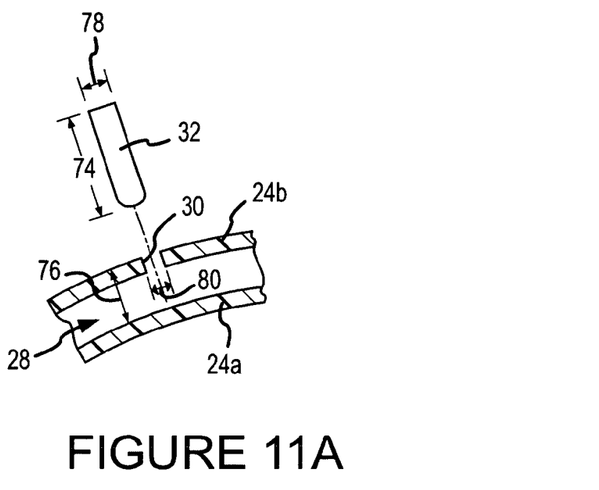
FIGS. 11A-11C are partial cross-sectional views of a double lens assembly illustrating a method for inserting a permeable plug in accordance with an embodiment of the invention.
Figure 11B:
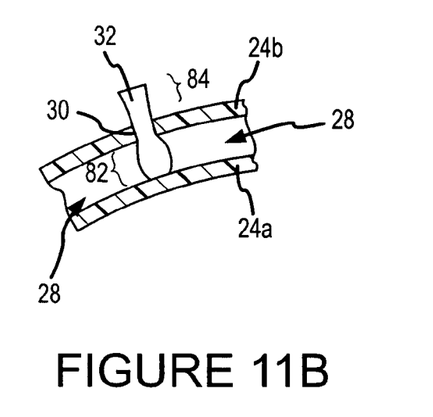
Figure 11C:
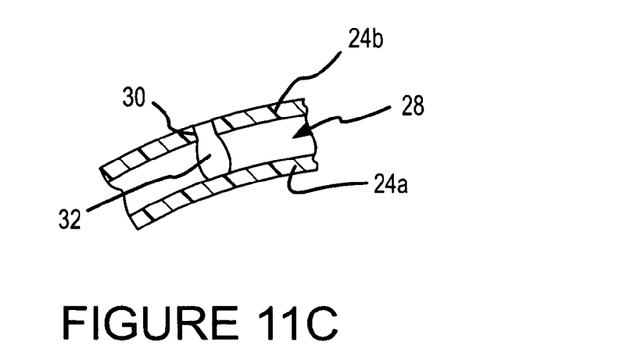

FIGS. 11A-11C illustrate a method for inserting a plug 32, such as is illustrated in FIGS. 3A and 3B. A plug 32 according to the illustrated method may have a length 74 that equals or exceeds the distance 76 between the outer surface of the outer lens 24b and the inner surface of the inner lens 24a. The width 78 of the plug 32 also preferably exceeds the diameter 80 of the aperture 30. As shown in FIG. 11B, the plug 32 is inserted within the aperture 30 such that a portion 82 projects into the air cavity 28. The plug 32 may be inserted such that the plug 32 abuts the inner surface of the inner lens 24a. As shown in FIG. 11C, the portion 84 of the plug 32 projecting from the outer surface of the outer lens 24b has been trimmed such that the plug 32 is substantially flush with the outer lens 24b.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An eye shield comprising:
    first and second lenses each having an inner and an outer surface, the inner surface of the first lens facing the inner surface of the second lens, the first and second lenses defining a first air cavity therebetween;
    a shroud extending along a perimeter of the first lens and extending outwardly from the outer surface of the first lens, the shroud and the outer surface of the first lens operable to cooperate with a wearer's face to define a second air cavity;
    a vent formed in the second lens to allow air into the first cavity; and
    a plug positioned in the vent and having at least a portion that extends into the vent, the plug comprising a liquid impermeable and gas permeable material positioned to obstruct at least a portion of the vent.

2. The eye shield of claim 1, wherein the material extends substantially completely through the second lens.

3. The eye shield of claim 1, wherein the material secures to the outer surface of the second lens.

4. The eye shield of claim 1, wherein the plug extends into the first air cavity.

5. The eye shield of claim 4, wherein the plug abuts the inner surface of the first lens.

6. The eye shield of claim 4, wherein the plug comprises a core and a sheathe extending around the core and wherein the material forms one of the sheathe and the core and the other of the sheathe and core comprises a resilient member.

7. The eye shield of claim 1, wherein the material comprises polytetrafluoroethylene.

8. The eye shield of claim 1, wherein the material comprises sintered polyethylene.

9. The eye shield of claim 8, wherein the sintered polyethylene comprises pores of between about 5 and 25 microns.

10. The eye shield of claim 1, further comprising a seal extending along the perimeter of the first lens and contacting the inner surfaces of the first and second lens.

11. The eye shield of claim 10, wherein the seal comprises an adhesive.

12. The eye shield of claim 11, wherein the seal comprises silicone.

13. An eye shield comprising:
    first and second lenses each having an inner and an outer surface, the inner surface of the first lens facing the inner surface of the second lens, at least one of the first and second lenses defining a vent extending therethrough;
    a seal extending along the perimeter of the first and second lenses, the first and second lenses and the seal defining an air cavity;
    a plug positioned within the vent, the plug comprising a liquid impermeable and gas permeable material to allow air to enter the air cavity and prevent liquid from entering the air cavity; and
    an expansion member extending at least partially into the plug effective to urge the plug outwardly from the expansion member.

14. The eye shield of claim 13, wherein the vent is formed in the second lens.

15. The eye shield of claim 13, wherein the plug extends substantially completely through the second lens.

16. The eye shield of claim 13, wherein the plug extends into the air cavity.

17. The eye shield of claim 16, wherein the plug abuts the inner surface of the first lens.

18. The eye shield of claim 13, wherein the plug comprises sintered polyethylene.

19. The eye shield of claim 18, wherein the sintered polyethylene has pores of between about 5 and 25 microns.

20. The eye shield of claim 13, wherein the seal comprises an adhesive.

21. The eye shield of claim 20, wherein the seal comprises silicone.

22. An eye shield comprising:
    first and second lenses each having an inner and an outer surface, the inner surface of the first lens facing the inner surface of the second lens, the first lens defining a vent extending therethrough;
    a seal extending along the perimeter of the first and second lenses, the first and second lenses and the seal defining an air cavity;
    a resilient member positioned within the vent; and
    a permeable member captured between the resilient member and the first lens, the permeable member comprising a liquid impermeable and gas permeable material, the vent and permeable member defining an air channel effective to allow air transfer with the air cavity.

23. The eye shield of claim 22, wherein the permeable member is captured between the resilient member and an outer surface of the first lens.

24. The eye shield of claim 23, wherein the permeable member comprises an aperture extending therethrough and wherein the resilient member is positioned within the aperture.

25. The eye shield of claim 24, wherein the resilient member comprises a shaft having at least one air channel formed therein and a cap secured to the shaft, the permeable member captured between the cap and the outer surface of the first lens.

26. The eye shield of claim 24, wherein the permeable member contacts a convex surface of the first lens.

27. A method for forming goggles comprising:
    positioning a semi liquid adhesive along a perimeter of a first lens;
    positioning a second lens having a vent formed therein over the first lens and in contact with the adhesive, the second lens being distanced from the first lens;
    curing the adhesive; and
    obstructing the vent with a liquid impermeable and gas permeable material that extends into a cavity defined by the second lens being distanced from the first lens.

28. The method of claim 27, further comprising positioning a plug within the vent.

29. The method of claim 28, wherein positioning the plug within the vent comprises inserting a permeable member within the vent and inserting an expansion member into the permeable member, the expansion member urges the permeable member outwardly against the vent.

30. The method of claim 29, wherein the permeable member comprises a substantially non-resilient material.

31. The method of claim 30, wherein the permeable member comprises sintered polyethylene.

32. An eye shield comprising:
   first and second lenses each having an inner and an outer surface, the inner surface of the first lens facing the inner surface of the second lens, the first and second lenses defining a first air cavity therebetween;
   a shroud extending along a perimeter of the first lens, the shroud and the outer surface of the first lens operable to cooperate with a wearer's face to define a second air cavity; and
   at least one aperture formed in the second lens, the aperture having a diameter equal to or less than 25 microns.

33. The eye shield of claim 32, wherein the aperture has a diameter equal or less than 15 microns.

34. The eye shield of claim 33, wherein the aperture has a diameter equal or less than 5 microns.

35. The method of claim 28 wherein positioning a plug in the vent comprises inserting a permeable member within the vent and inserting an expansion member into the permeable member.

* * * * *